United States Patent [19]
Horikita et al.

[11] Patent Number: 4,923,812
[45] Date of Patent: May 8, 1990

[54] PROCESS FOR PRODUCING ERYTHRITOL

[75] Inventors: Hiroyuki Horikita, Chita; Nobuo Hattori; Yahei Takagi, both of Nagoya; Gaku Kawaguchi, Gyoda; Toshihiro Maeda, Zama, all of Japan

[73] Assignee: NGK Insulators, Ltd., Japan

[21] Appl. No.: 373,694

[22] Filed: Jun. 29, 1989

Related U.S. Application Data

[63] Continuation of Ser. No. 300,973, Jan. 24, 1989, abandoned.

[30] Foreign Application Priority Data

Feb. 3, 1988 [JP] Japan ................. 63-24813

[51] Int. Cl.$^5$ .................... C12P 7/18; C12R 1/645
[52] U.S. Cl. ................... 435/158; 435/813; 435/818; 435/911
[58] Field of Search ............... 435/158, 813, 818, 911

[56] References Cited

U.S. PATENT DOCUMENTS 2,986,495  5/1961  Onishi .................. 435/158
3,756,917  9/1973  Dezeeuw et al. ........ 435/158

FOREIGN PATENT DOCUMENTS 0557492   5/1958  Canada ................. 435/158
0613267   1/1961  Canada ................. 435/158
0136802   4/1985  European Pat. Off. .... 435/158
0136803   4/1985  European Pat. Off. .... 435/158
0136804   4/1985  European Pat. Off. .... 435/158
0136805   4/1985  European Pat. Off. .... 435/158
0003546   6/1962  Japan ................... 435/158
60-110296 6/1985  Japan .
1031082   2/1986  Japan ................... 435/158
1031091   2/1986  Japan ................... 435/158
2096090   5/1987  Japan ................... 435/158

OTHER PUBLICATIONS

"Erythritol Production by a Yeastlike Fungus", G. J. Hanjny et al., Applied Microbiology, vol. 12, No. 3, May 1964, pp. 240–246.
"Continuous Culture with Complete Cell . . . ", Olee Holst et al., Applied Microbiology and Biotechnology, vol. 23, 1985, pp. 10–14.
"Huge Plant for Ethanol and HFCS", Charles E. Morris, Food Engineering, Jun. 1983, pp. 107–112.
"Ethanol Production by Cell Recycling with Hollow Fibers", Yoshinori Nishizawa et al., J. Ferment. Tech., vol. 61, No. 6, 1983, pp. 599–605.
"High Concentration Cultivation . . . ", Masayuki Taniguchi et al., Applied Microbiology and Biotechnology, vol. 25, 1987, pp. 438–441.
"A Filter Fermenter-Apparatus and Control Equipment", Milan Dostalek et al., Biotech. and Bioengineering, vol. XXIV, 1982, pp. 2077–2086.

Primary Examiner—Herbert J. Lilling
Attorney, Agent, or Firm—Arnold, White & Durkee

[57] ABSTRACT

A process is disclosed for continuously producing erythritol by cultivating erythritol-producing microorganisms under aerobic conditions. The process comprises the steps of: maintaining the concentration of dissolved oxygen in a culture broth in a fermentation tank at not less than 0.2 ppm; separating a part of the culture broth into a concentrated liquid in which the concentration of cells is increased and a clarified liquid by a cell separator; returning the concentrated liquid to the fermentation tank; controlling an amount of the clarified liquid to be extracted outside an erythritol-producing system and an amount of the culture broth and/or the concentrated liquid to be extracted outside the producing system such that the concentration of the cells in the culture broth in the fermentation tank may be kept in a range from 40 to 200 g/l when calculated as a weight of dried cells; and recovering erythritol from the clarified liquid.

The clarified liquid containing erythritol may be separated from the culture broth by a cell separator arranged inside the fermentation tank, and the extracting amount of the erythritol-containing clarified liquid separated by the cell separator and an amount of the culture broth to be extracted may be controlled such that the concentration of the cells in the culture broth may be kept at 40 to 200 g/l when calculated as a weight of dried cells.

2 Claims, 3 Drawing Sheets

PROCESS FOR PRODUCING ERYTHRITOL

This is a continuation of application Serial No. 07/300,973 filed January 24, 1989, now abandoned.

BACKGROUND OF THE INVENTION (1) Field of the Invention

The present invention relates to a process for producing erythritol as a kind of polyols by using erythritol-producing microorganisms.

Erythritol is also called erythrit, and has the following characteristics:

| | |
|---|---|
| Melting point: | 122° C., |
| Decomposed temperature: | 329° C., |
| Chemical formula: | $CH_4O_4H_{10}$, |
| Rational formula: | $CH_2OH-CHOH-CHOH-CH_2OH$. |
| Chemical structure: | 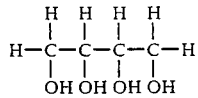 |

Erythritol is a kind of sugaralcohols, and demand for erythritol has recently been increasing due to its sweetness twice that of sucrose.

(2) Related Art Statement

Processes have already been known for producing erythritol by using erythritol-producing microorganisms. For example, Japanese Patent Application Laid-open Nos. 60-110,295 and 61-31,091 disclose processes for producing erythritol from fermentable saccharides such as glucose with use of the erythritol-producing microorganisms, and U.S. Patent No. 3,756,917 discloses a process for producing erythritol from hydrocarbons. However, as described in these publications, there have heretofore been employed batch type producing processes in which a substrate and erythritol-producing microorganisms are charged into a fermentation tank and fermented for 1 to 2 weeks, a broth is taken out from the tank, and a reaction product is separated therefrom. Therefore, the conventional processes have problems in that the volume of the producing apparatus is great, that the production cost is high, and that the production rate of the erythritol cannot be increased to not less than 1.5 g/l.H. In order to solve the above problems, the present inventors have tried a continuous fermentation process in which a liquid inside a tank is extracted, while a substrate is continuously charged thereinto. However, since it was difficult to maintain the concentration of cells at a high level due to much flowout of the cells, the erythritol production rate could not greatly be increased.

SUMMARY OF THE INVENTION

The present invention has been accomplished to solve the above-mentioned conventional problems, and to provide a process for producing erythritol of which production rate can be assured at a high level by a compact apparatus.

According to a first aspect of the present invention, there is a provision of a process for continuously producing erythritol by cultivating erythritol-producing microorganisms under aerobic conditions, which comprises the steps of: maintaining the concentration of dissolved oxygen in a culture broth inside a fermentation tank at not less than 0.2 ppm; separating a part of the culture broth into a concentrated liquid in which the concentration of cells is increased and a clarified liquid by a cell separator; returning said concentrated liquid to the fermentation tank; controlling an amount of the clarified liquid to be extracted outside an erythritol-producing system and an amount of the culture broth and/or the concentrated liquid to be extracted outside the system such that the concentration of the cells in the culture broth in the fermentation tank may be kept in a range from 40 to 200 g/l when calculated as a weight of dried cells; and recovering erythritol from the clarified liquid.

According to a second aspect of the present invention, there is a provision of a process for continuously producing erythritol by cultivating the erythritol-producing microorganisms under aerobic conditions, which comprises the steps of: maintaining the concentrating of dissolved oxygen in a culture broth in a fermentation tank at not less than 0.2 ppm; separating a clarified liquid containing erythritol from the culture broth by a cell separator arranged inside the fermentation tank; controlling an extracting amount of the erythritol-containing clarified liquid separated by the cell separator and an amount of the culture broth to be extracted such that the concentration of the cells in the culture broth in the fermentation tank may be kept in a range from 40 to 200 g/l when calculated as a weight of dried cells; and recovering erythritol from the clarified liquid.

According to the present invention, the production rate of erythritol can greatly be increased.

These and other objects, features, and advantages of the invention will be appreciated upon reading of the following description of the invention when taken in conjunction with the attached drawings, with the understanding that some modifications, variations and changes of the same could be made by the skilled person in the art to which the invention pertains without departing from the spirit of the invention or the scope of claims appended hereto.

BRIEF DESCRIPTION OF THE ATTACHED DRAWINGS

For a better understanding of the invention, reference is made to the attached drawings, wherein.

DETAILED DESCRIPTION OF THE INVENTION

The present invention will be explained in more detail below.

Figure 1:
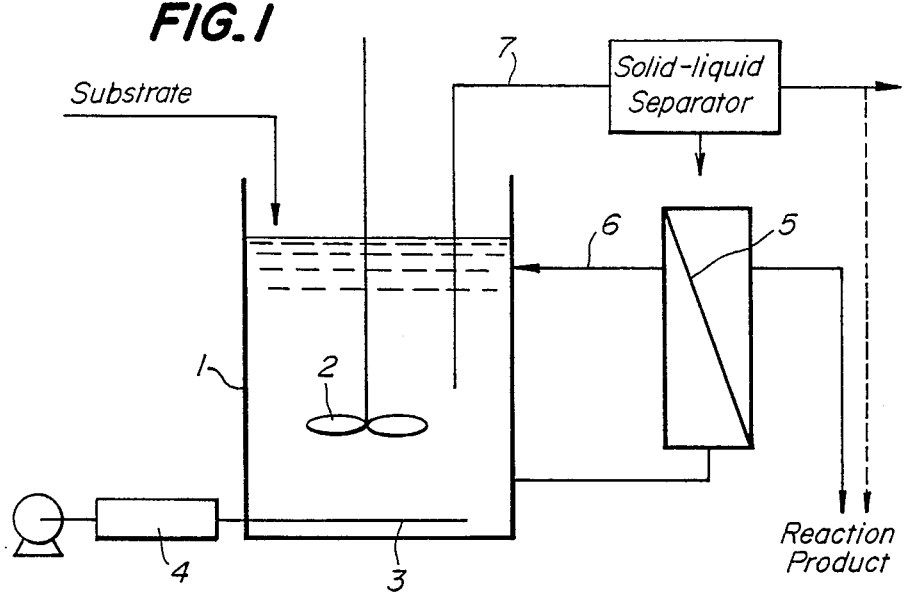
FIG. 1 is a sectional view of an apparatus for use in the present invention.

In the first aspect of the present invention, as shown in FIG. 1, a substrate is continuously charged into a fermentation tank together with an inorganic salt such as $KH_2PO_4$, $MgSO_4$, $K_2SO_4$, $CaSO_4$, $FeSO_4$, $MnSO_4$, $ZnSO_4$, $(NH_4)_2HPO_4$, or $CaCl_2$, a nitrogen source such as $(NH_4)_2SO_4$, urea, $NH_4NO_3$, or $NH_4Cl$, a nutrient source such as $(NH_4)_2SO_4$, urea $NH_4NO_3$, or $NH_4Cl$, a nutrient source such as corn steep liquor, yeast extract, peptone, various amino acids, thiamine, or bitotin, while a liquid inside the fermentation tank is stirred by a stirrer 2 under blowing of air clarified with an air filter 4 thereinto through an air feeding pipe 3 at the bottom. Thereby, fermentation is continuously effected with erythritol-producing microorganisms in the liquid inside the tank. The concentration of dissolved oxygen is kept at not less than 0.2 ppm by blowing air at a rate of 0.5 to 2 $m^3/m^3$. min. In FIG. 1, a reference numeral 5 is a cell separator arranged outside the fermentation tank. The liquid inside the fermentation tank is separated into a concentrated liquid containing the erythritol-producing microorganisms and a clarified erythritol liquid containing no or a small amount of the erythritol-producing microorganisms by the cell separator 5. The concentrated liquid is returned into the fermentation tank 1 through a line 6. On the other hand, the clarified liquid is extracted outside the fermentation system as a fermented product. When the erythritol-producing microorganisms are prevented from flowing outside the fermentation tank in this manner, the concentration of the cells in the liquid inside the fermentation tank gradually increases. Consequently, the production rate of erythritol lowers, and the cells are difficult to separate in the cell separator. Therefore, according to the present invention, a part of the liquid inside the fermentation tank is extracted outside through an extracting line 7 to control the amount of the cells in the tank. Thus, the concentration of the cells is adjusted mainly by extracting a part of the culture broth outside the system by using the extracting pipe 7. However, it may be that a part of the concentrated liquid is extracted outside through the above-mentioned line 6. The thus extracted culture broth may be separated into a clarified liquid and a cell-concentrated liquid by the solid-liquid separator so that the clarified liquid may be utilized to obtain a fermented product.

Next, various constituent features of the present invention will more concretely be explained.

Figure 3:
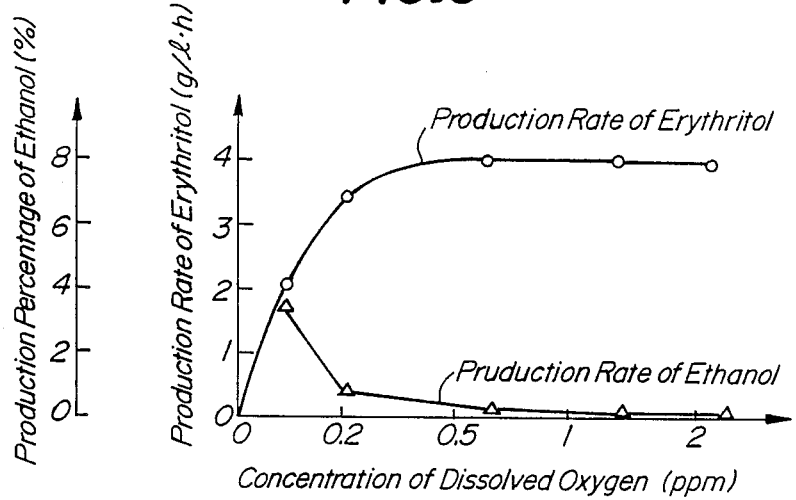
FIG. 3 is a graph showing the relationship between the concentration of dissolved oxygen and the production rate of erythritol.

The reason why the concentration of the dissolved oxygen in the culture broth inside the fermentation tank is limited to not less than 0.2 ppm is that the fermentation reaction is effected under aerobic conditions, and that as shown in FIG. 3, since ethanol is produced in anaerobic fermentation if the concentration is less than 0.2 ppm, the production rate of erythritol lowers. A graph shown in FIG. 3 was obtained by effecting experiments under the conditions that the concentration of the cells was kept at 100 g/l, while the concentration of oxygen dissolved was varied by changing the amount of air blown to various levels.

As the cell separator, use may be made of a liquid cyclone to be used in ordinary solid-liquid separation and a solid-liquid separator such as a precipitation separating tank. Noting the size of the erythritol-producing microorganisms, it is preferable to use a separated plate type (De Laval type) or inclined type (super decant type) centrifugal precipitation device which can continuously separate the cells from the liquid by utilizing centrifugal forces of 1,000 G to 10,000 G, a microfiltration membrane, or a ultra filtration membrane.

As a separating membrane of the membrane separator employed as the cell separator, it is preferable to use a microfiltration membrane having pores of not more than 1 $\mu m$ in diameter or a ultra filtration membrane having a cut-off molecular weight of not less than 10,000 for the purpose of assuredly separating the cells. If the pore diameter is more than 1 $\mu m$, the pores of the filter are likely to be plugged by the yeast, etc. Consequently, a permeation flux tends to lower in a short time. Similarly, if the fractionation molecular weight is not more than 10,000, the permeation flux drops. Thus, advantageous separation becomes impossible.

Figure 4:
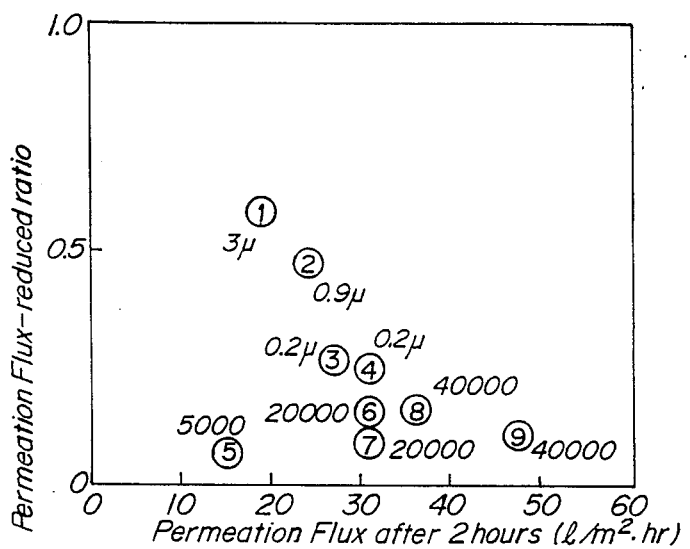
FIG. 4 is a graph showing results of a variety of separating membranes in characteristic-checking tests.

FIG. 4 show results obtained by testing characteristics of such separation membranes with use of a flat membrane type tester. Reference numerals 1 through 4 denote filters having diameters of pores (3 $\mu \sim 0.2$ $\mu$)allotted thereto in FIG. 4, respectively, and reference numerals 5 through 9 show those having allotted a cut-off molecular weights (5,000~40,000), respectively. The material of each of the filters is as follows:

①, ④ ... metal
②, ③ ... ceramic
⑤, ⑥, ⑦, ⑨ ... polyacryl nitrile
⑧ ... polyester sulfone In the tests, a liquid containing 94 g/l of cells, 19% of erythritol and 2% of glucose was continuously flown under pressure of 1 $kg/cm^2$ for 2 hours. Evaluations were made based on the permeation flux and the permeation flux-reduced rate "m" at the time of 2 hours from the flowing. The permeation flux-reduced rate "m" were determined by the following equation.

$$J/J_0 = (T/T_0)^{-m}$$

in which J and $J_0$ a are a permeation flux after $T_0$ hours and the permeation flux at initial $T_0$ hours, respectively.

As mentioned above, the liquid inside the fermentation tank can be separated into the cell-containing concentrated liquid and the filtrate containing erythritol by using appropriate separation membrane 5.

Figure 5:
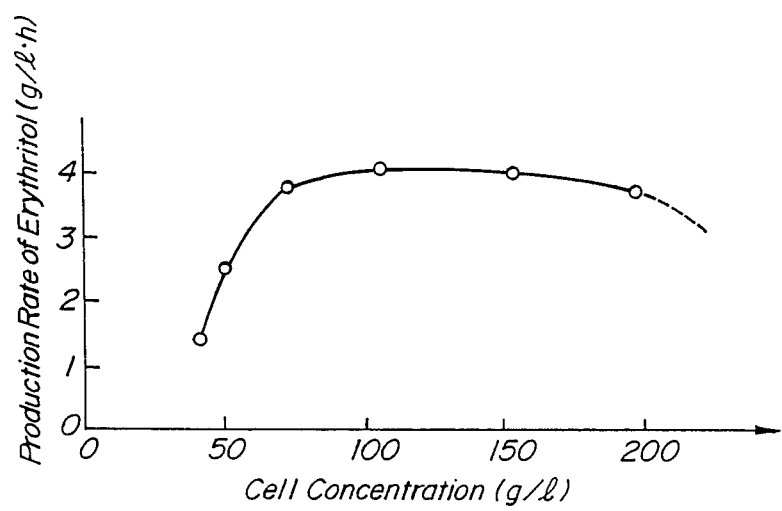
FIGS. 5 is a graph showing the relationship between the concentration of cells and the production rate of erythritol.

The amount of the liquid extracted from the fermentation tank through the line 7 is determined such that the amount of the cells in the fermentation tank may be kept at 40 to 200 g/l when calculated as a dried cell weight. When the fermentation system is normally operated, the amount of the liquid to be extracted is set at not greater than that of the clarified liquid to be extracted. As shown in FIG. 5, if the amount of the cells is less than 40 g/l, the cells becomes insufficient to lower the production rate of erythritol. On the other hand, if the amount is more than 200 g/l, the cells become excessive to also lower the production rate of erythritol require a greater amount of oxygen, and drop the production rate per unit power. For this reason, the amount of the cells is set preferably at 40 to 200 g/l, more preferably 80 to 150 g/l.

A graph shown in FIG. 5 was obtained under the following conditions:
Substrate:
  glucose 40%, yeast extract: 2%,
Separation membrane:
  ceramic porous membrane (pore diameter 0.2 $\mu m$),
Fermentation liquid amount:
  fermentation tank volume 2.5 l, circulating line 1.5 l,
Blown air amount:
  1-2 $m^3/m^3$.min,
Substrate feed amount:
  2 l/day (residence time: 48 hours)

As is clear from the foregoing explanation, according to the present invention, it is possible to remarkably increase the production rate of erythritol from a conventional rate of 1.5 g/l·H to 4.0 g/l·H.

Figure 2:
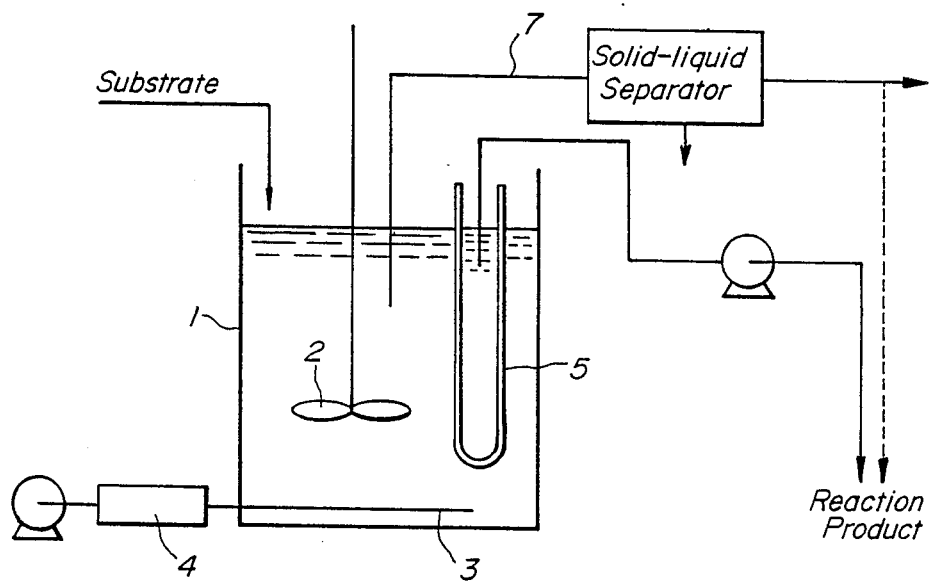
FIG. 2 is a sectional view of a modification of FIG. 1.

FIG. 2 shows a fermentation system to be used in the second aspect of the present invention. A separating membrane 5 is designed in a tubular type, which is arranged inside a fermentation tank 1. In this case, the line 6 in FIG. 1 can be omitted. Further, in the embodiment of FIG. 2, a filtering pressure may be applied to the filtering membrane 5 by sealing an upper face of the fermentation tank 1 and pressurizing the liquid surface.

In the following, examples of the present invention will be explained below. Examples 1 and 2 belong to the first aspect of the present invention, and Example 3 to the second aspect of the invention.

EXAMPLE 1

Erythritol-producing microorganisms (Aureobasidium sp. SN-G42) was cultivated in 200 ml of a liquid culture medium containing 30% (w/v) of glucose and 1% (w/v) of yeast extract at 35° C. for 72 hours under shaking, which was added to 3.8 l of an initial culture medium containing 40% (w/v) of glucose and 2% (w/v) of yeast extract. The mixture was batch cultivated at 35° C. and a stirring rate of 800 rpm while air was being passed at 1 vvm. When the concentration of glucose in the culture medium reached 5% or less, a circulating pump directly connected to a ceramic membrane having pores of 0.2 μm was started, and a substrate having the same composition as the initial culture medium was begun to be fed at 83.3 ml/h. While a cultivation filtrate was extracted through the ceramic membrane at the same rate, cultivation was continuously effected. When the concentration of the cells in the fermentation tank reached 100 g (dried weight)/l, the cultivation filtrate-extracting rate was dropped to 42 ml/h and at the same time, the culture broth was extracted directly from the fermentation tank at a rate of 41.3 ml/h, so that the concentration of the cells might be kept constant. Thereafter, the continuous filtration-cultivation was effected, while the concentration of the cells was kept at about 100 g/l. During the cultivation, the average production rate of erythritol was 4.2 g/l.h.

EXAMPLE 2

1.5 l of seed cultures of erythritol-producing microorganisms (Aureobasidium sp. SN-G42), which had been cultivated in a culture broth containing 30% (w/v) of glucose and 0.675% (w/v) of yeast extract in a rotary shaker at 30° C. for 72 hours under shaking, were added to 25 l of an initial culture medium which was placed in a 50 l fermentation tank and which contained 40% (w/v) of glucose and 6.7% (w/v) of corn steep liquor and was adjusted at pH 4.2. The mixture was cultivated under sufficiently aerobic conditions of 35° C., forcedly stirring at 600 rpm and pressure of 0.5 g/cm$^2$, while aseptic air was being fed at a rate of 37.5 l/min. Since the concentration of glucose in the culture medium reached 2% (w/v) after 90 hours, a substrate having the same composition as that of the initial culture medium was started to be fed. The feed rate of the substrate was then kept constant at 0.58 l/h. In order to prevent elevation of the liquid surface level inside the fermentation tank, the liquid was extracted and fed from the fermentation tank at 1.74 l/h to a separated plate type (De Laval type) centrifugal precipitation device. The cells were separated from the liquid by centrifugal forces of 6,000 G, 0.58 l/h of a clarified liquid was extracted outside the system as a product, and the remaining cell-concentrated liquid was returned to the fermentation tank. From the time when the concentration of the cells inside the fermentation tank reached 100 g/l when calculated as a dried cell weight, the feed rate for the centrifugal precipitation device was dropped to 0.96 l/h, and at the same time the amount of the clarified liquid extracted from the centrifugal separator was reduced to 0.32 l/h. On the other hand, in order to keep the concentration of the cells inside the fermentation tank, the culture broth inside the fermentation tank was directly extracted at 0.26 l/h. The fermentation system reached a stable state 250 hours after the cultivation, and the cultivation was further continued for 150 hours. After the system reached the stable state, the average concentration of erythritol in a mixed liquid consisting of 0.32 l/h of the clarified liquid and 0.26 l/h of the extracted culture broth was 194 g/l, and the yield and the production rate of erythritol were 48.5% and 4.5 g/l/h, respectively.

EXAMPLE 3

Erythritol-producing microorganisms (Aureobasidium sp. SN-G42) were cultivated in 200 ml of a liquid culture medium placed in a 500 ml conical flask and containing 30% (w/v) of glucose and 1% (w/v) of yeast extract at 35° C. for 48 hours under shaking, which was added to a 7 vol l fermentation tank. The fermentation tank contained 3 l of a culture medium containing 40% (w/v) of glucose and 8% (w/v) of corn steep liquor, and was equipped with a cell separator (denoted by a reference numeral 5 in FIG. 2). Then, batch cultivation was effected under conditions of 35° C., pH 4.2 and a stirring rate of 1,000 rpm, while air was passed at 1 vvm. When the concentration of glucose in the culture medium reached 5% or less after 70 hours, a culture medium containing 40% (w/v) of glucose and 8% (w/v) of corn steep liquor was fed at 83.3 ml/h as a substrate. While a cultivation filtrate was also extracted using a filter at the same rate, continuous cultivation was effected. When the concentration of the cells reached 98.5 g (dried cell weight)/l after 113 hours following the cultivation, the extracting rate of the cultivation filtrate was dropped to 41.65 ml/h and at the same time the culture broth was extracted directly from the fermentation tank at a rare of 41.65 ml/h so as to keep the concentration of the cells constant. Then, cultivation was continuously effected for 167 hours, while the concentration of the cells was kept at 100 g/l. During the cultivation, the average production rate and the yield of erythritol were 5.1 g/l/h and 50%, respectively.

As is clear from the foregoing explanation, the present invention has succeeded in raising the production rate of erythritol to twice the conventional rate while maintaining the concentration of the cells at an appropriate level, by controlling the concentration of dissolved oxygen, separating the cells, and extracting the culture broth inside the fermentation tank to the outside. In addition, according to the present invention, the entire fermentation apparatus can be made compact with no need to use a large scale of a fermentation tank as in the conventional batch type production. Therefore, the present invention can greatly contribute to industrial developments as the erythritol-producing process, which sweeps out the problems of the prior art.

What is claimed is:

1. A process for continuously producing erythritol by cultivating erythritol-producing microorganisms under aerobic conditions, said process comprising the steps of:

maintaining a concentration of dissolved oxygen in a culture broth inside a fermentation tank at not less than 0.2 ppm;

separating a part of the culture broth into a concentrated liquid in which a concentration of cells is increased and a clarified liquid by a cell separator;

returning said concentrated liquid to the fermentation tank;

controlling an amount of said clarified liquid to be extracted outside an erythritol-producing system and an amount of the culture broth and/or the concentrated liquid to be extracted outside the producing system such that the concentration of the cells in the culture broth in the fermentation tank may be kept in a range from 40 to 200 g/l when calculated as a weight of dried cells;

and recovering erythritol from said clarified liquid.

2. A process for continuously producing erythritol by cultivating erythritol-producing microorganisms under aerobic conditions, said process comprising the steps of:

maintaining a concentration of oxygen dissolved in a culture broth in a fermentation tank at not less than 0.2 ppm;

separating a clarified liquid containing erythritol from the culture broth by a cell separator arranged inside the fermentation tank;

controlling an extracting amount of said clarified liquid separated by the cell separator and an amount of the culture broth to be extracted such that the concentration of the cells in the culture broth in the fermentation tank may be kept in a range from 40 to 200 g/l when calculated as a weight of dried cells;

and recovering erythritol from said clarified liquid.

* * * * *

UNITED STATES PATENT AND TRADEMARK OFFICE
CERTIFICATE OF CORRECTION

PATENT NO. : 4,923,812
DATED : May 8, 1990
INVENTOR(S) : PROCESS FOR PRODUCING ERYTHRITOL

It is certified that error appears in the above-identified patent and that said Letters Patent is hereby corrected as shown below:

ON TITLE PAGE:
Page 1, [73] Assignee: should read --NGK Insulators, Ltd., Japan; Nikken Chemicals Co., Ltd., Japan; and Mitsubishi Kasei Corporation, Japan--

Signed and Sealed this

Thirteenth Day of August, 1991

Attest:

HARRY F. MANBECK, JR.

Attesting Officer

Commissioner of Patents and Trademarks